Figure 1:
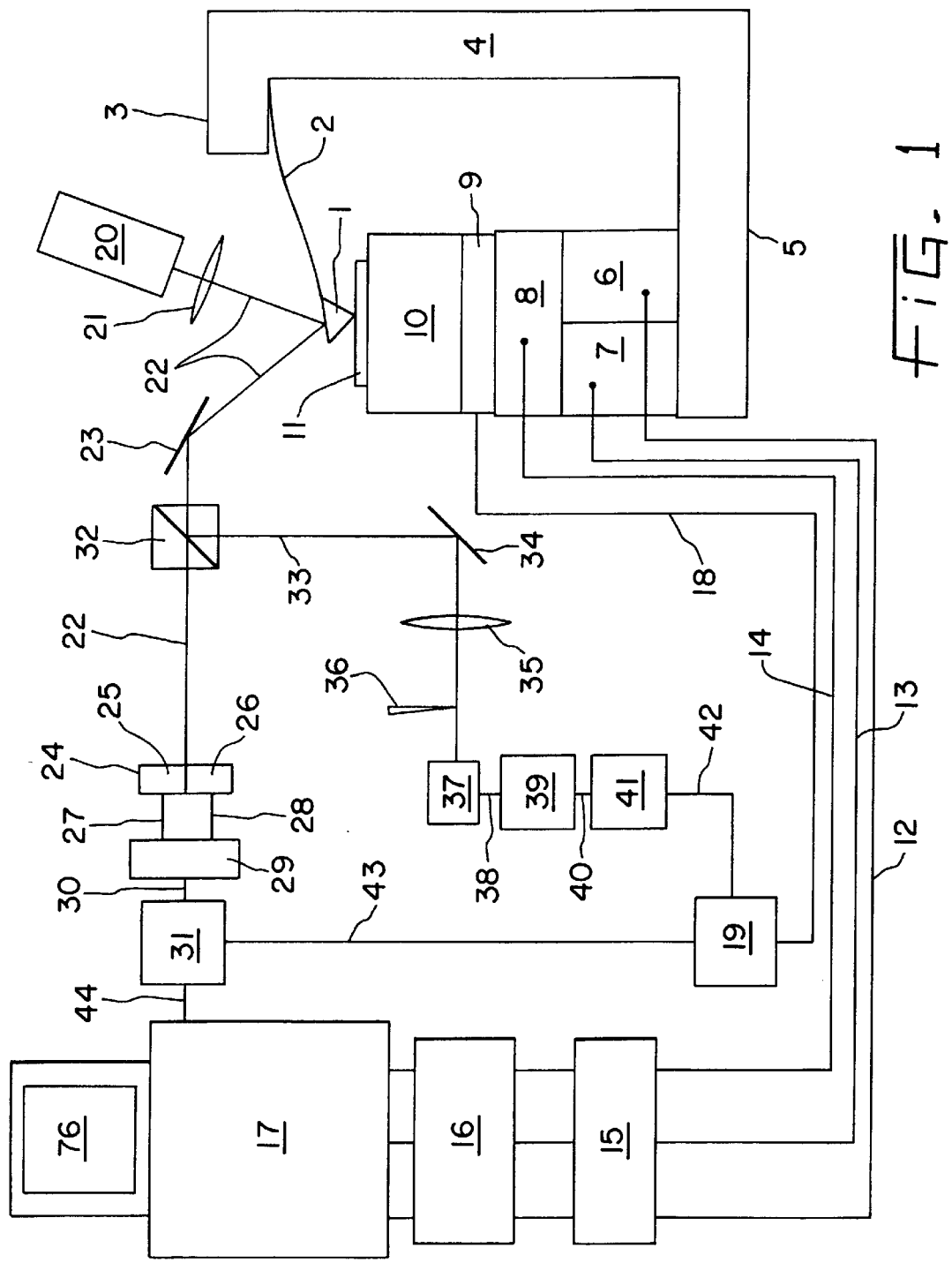

United States Patent [19]
Arnold et al.

[11] Patent Number: 5,852,233
[45] Date of Patent: Dec. 22, 1998

[54] ACOUSTIC MICROSCOPE WITH A CONTROL AND DATA CAPTURING DEVICE

[75] Inventors: Walter Arnold; Ute Rabe, both of Saarbrucken, Germany

[73] Assignee: Fraunhofer-Gesellschaft Zur Forderung der Angewandten Forschung E.V., Germany

[21] Appl. No.: 886,929

[22] Filed: Jul. 2, 1997

Related U.S. Application Data

[62] Division of Ser. No. 545,849, Nov. 13, 1995, Pat. No. 5,675,075.

[30] Foreign Application Priority Data

Jul. 26, 1993 [DE] Germany ............................ 43 24 983.3
Jun. 30, 1994 [WO] WIPO ...................... PCT/DE94/00765

[51] Int. Cl.⁶ .............................. G01B 9/04; G01B 11/30
[52] U.S. Cl. .......................................................... 73/105
[58] Field of Search ................................ 73/105; 250/306

[56] References Cited

U.S. PATENT DOCUMENTS

| | | | |
|---|---|---|---|
| 4,941,753 | 7/1990 | Wickramasinghe | 374/120 |
| 5,019,707 | 5/1991 | Chiu et al. | 250/306 |
| 5,164,791 | 11/1992 | Kubo et al. | 250/306 X |
| 5,166,516 | 11/1992 | Kajimura | 250/234 |
| 5,260,824 | 11/1993 | Okada et al. | 73/105 X |
| 5,267,471 | 12/1993 | Abraham et al. | 73/105 |
| 5,298,975 | 3/1994 | Khoury et al. | 73/105 X |
| 5,315,373 | 5/1994 | Kubo et al. | 73/105 X |
| 5,319,977 | 6/1994 | Quate et al. | 250/306 X |
| 5,391,871 | 2/1995 | Matsuda | 73/105 X |
| 5,503,010 | 4/1996 | Yamanaka | 73/105 |

FOREIGN PATENT DOCUMENTS

| | | |
|---|---|---|
| 0 383 323 | 8/1990 | European Pat. Off. . |
| WO 89/12805 | 12/1989 | WIPO . |

OTHER PUBLICATIONS

Kikuta et al., "Force Microscopy Using Common–Path Optical–Heterodyne Interferometer", Japanse Journal of Applied Physics, Part I, vol. 30, No. 03, Mar. 1991, pp. 587–590.

Nonnenmacher et al., "Attractive Mode Force Microscopy Using a Feedback–Controlled Fiber Interferometer", Rev. Sci. Instrum., vol. 63, No. 11, Nov. 1992, pp. 5373–5376.

Nonlinear Detection of Ultrasonic Vibrations in an Atomic Force Microscope O. Kolosov et al, JPN.J.Appl.Phys., vol 32 (1993) Part 2, No. 8A, 22–25.

Probing of Acoustic Surface Perturbtions by Coherent Light, R. L. Whitman et al, Applied Optics, Aug. 1969, vol. 8, No. 8, 1567–1576.

Single–Tube Three Dimensional Scanner for Scanning Tunneling Microscopy, G. Binning et al, Rev.Sci.Instrum.57(8), Aug. 1986, 1688–1689.

Scanning Microdeformation Microscopy, B. Cretin et al, Appl.Phys.Lett.62(8), 22 Feb. 1993, 829–831.

(List continued on next page.)

Primary Examiner—Daniel S. Larkin
Attorney, Agent, or Firm—Baker & Daniels

[57] ABSTRACT

An acoustic microscope allowing both the topography and the elasticity of a sample to be measured at the same time. To this end the displacement of a cantilever with a tip is measured by the deflection of a laser beam. In order to measure the topography, the average deviation of the tip is held constant by a regulation circuit. The regulation circuit consists of a split-photodiode which supplies a neutral signal to the output of a normalizing amplifier which delivers a neutral value. Deviations from this neutral signal are compensated by a z-electrode of a piezocrystal. The elastic properties of the sample are measured by coupling ultrasound into the sample by means of a transducer and the high-frequency displacements of the cantilever with the tip are detected by a second detection device that consists of knife-edge detector and a fast photodiode. The detection device may also consist of a heterodyne time-of-flight interferometer or a capacitive detection scheme.

2 Claims, 4 Drawing Sheets

OTHER PUBLICATIONS

Capacitive Pickup Circuitry for Video Discs, R.C. Palmer et al, RCA Review, vol. 43, Mar. 1982, 194–211.

Nearfield Scanning Acoustic Microscopy, A. Kulik et al., Ecole Polytechnique Federale De Lausanne.

Akustische Mikroskopie, S. Boseck, Phys. Bl. 49 (1993) NR.6, 497–502.

Acoustic Microscopy Beyond the Diffraction Limit, An Application of Microfabrication, S. Akamine et al, 91CH2817, 1991 IIEEE, 857–859.

Optical Detection of Ultrasound, Jean–Pierre Monchalin, IEEE Transaction on Ultrasonics, vol. UFFC.33, No. 5, Sep. 1986, 485–499.

Acoustic Microscopy—1979 Lawrence W. Kessler et al, Proceedings of the IEEE, vol. 67, No. 4, Apr. 1979, 526–536.

Determination of Displacements in Ultrasonic Waves By Scanning Tunneling Microscopy, J. Heil et al, J.Appl.Phys. 64(4), 15 Aug. 1988, 1939–1944.

Detection of Surface Acoustic Waves By Scanning Tunneling Microscopy, W. Rohrbeck et al, Appl.Phys. A 52, 344–347 (1991).

High–Frequency Surface–Displacement Detection Using an STM as a Mixer Demodulator, K. Strozewski et al, Ultramicroscopy 42–44 (1992) 388–392.

Detection of Ultrasound Using a Tunneling Microscope, A. Moreau et al, J.Appl.Phys, 72(3), 1 Aug. 1992, 861–864.

Probing of Surface Acoustic Wave Fields By a Novel Scanning Tunneling Microscopy Technique, E. Chilla et al, Appl.Phys.Lett. 61 (26), 28 Dec. '92.

Tunneling Acoustic Microscope, K. Takata et al, Appl.Phys.Lett. 55 (17), 23 Oct. 1989, 1718–1720.

Using Force Moduation to Image Surface Elasticities With The Atomic Force Microscope, P. Maivald et al, University of California.

Scanned Probe Microscopes by H. Kumar Wickramasinghe Scientific American Oct. , 1989.

Tortonese, "Atomic Force Microscopy Using a Piezoresistive Cantilever", pp. 448–451.

ACOUSTIC MICROSCOPE WITH A CONTROL AND DATA CAPTURING DEVICE

This application is a division of Ser. No. 545,849 filed Nov. 13, 1995 now U.S. Pat. No. 5,675,075.

BACKGROUND OF THE INVENTION

The invention concerns an acoustic microscope for examination of a specimen, with a nib affixed to an elastic beam and arranged in the near-surface area of a specimen surface, with a supersonic transducer coupled to the specimen, with a device for positioning the specimen relative to the nib, where the nib has at time average a consistent distance from the surface, and with a control and data capturing device.

An acoustic microscope of this kind is known from WO 89/12805. On this acoustic microscope, a nib attached to a tuning fork is arranged in the near-surface area of a specimen surface. Forming an elastic beam, the tuning fork of piezoelectric quartz can be excited to mechanical vibrations by application of an electrical alternating voltage via electrodes attached to its shanks. These mechanical vibrations couple by way of the nib, as ultrasound, in the surface and, depending on the interaction between the vibrating nib and the specimen surface, lead on account of the attenuation of the vibration to a shift of the vibration frequency and/or the amplitude of the tuning fork as against a free vibration. The specimen and nib allow positioning relative to each other by means of a moving apparatus, the nib being at time average arranged at a consistent distance from the surface. A control and data capturing device serves the coordination of the data sensed by the nib in contingence on the relative position of the nib to the specimen.

In this acoustic microscope the tuning fork with the nib attached to it serves both as supersonic transmitter and also as sensor. Therefore, an electronic substraction of substantially equal values for the frequency and amplitude of the mechanical vibration must be carried out for obtaining the measured values, which subtraction is relatively prone to error. The result, notably with short measuring times per measuring point on the surface, is an unfavorable, poor signal-to-noise ratio. Owing to the resonant stimulation of the tuning fork in sustained operation, a scan of the topography of the surface, separate of sensing for instance elastic properties, can basically not be performed in the coupling area between the nib and the surface. A further provision with this acoustic microscope is stimulating the tuning fork preferably at its resonant frequency in the range of about 32 kHz, so that, while the amplitude is high in relation to the stimulating force, coupled-in interference vibrations cause in this frequency range as well excessively high interference amplitudes, which unfavorably affect the signal-to-noise ratio.

Another acoustic microscope is known from the publication "Scanning Microdeformation Microscopy," by B. Cretin and F. Sthal in the magazine "Applied Physics Letters" 62 pp 829 through 831 (1993). In this device, the vibrations of the nib at approximately 50 kHz produce at the resonant frequency of the elastic beam microdeformations on the specimen surface which induce an acoustic wave in the specimen. The acoustic wave allows detection by amplitude and phase relative to the vibrations of the nib, with a supersonic transducer. Plotting the amplitude and/or phase of the supersonic wave allows the generation of an image of the elastic properties of the specimen surface scanned by the nib, in contingence on the position of the nib. Possible also is detecting and imaging material inhomogeneities contained beneath the surface. The local resolution of this microscope ranges at around 10 μm.

With such an acoustic microscope it is possible to detect mechanically hard and soft areas of the specimen surface. But a topography of the specimen surface is possible only indirectly, by processing the supersonic signals received, and proves to be very difficult, notably with relatively complex semiconductor topographies. With modern semiconductor structures ranging in the order of a few μm, this microscope cannot be used for high-resolution examinations on such specimens.

A further disadvantage of this acoustic microscope is the relatively low signal-to-noise ratio. The vibrating nib acts as a point source, so that the amplitude of the ultrasound after passage through the specimen, in addition to the attenuation in the medium of propagation, due to the spherical wave characteristic of the broadcast ultrasound, is very low at the point of detection. Therefore, amplification of the signal detected by the supersonic transducer is provided for, using a lock-in amplifier, in order to improve the signal-to-noise ratio. However, this entails a relatively long measuring time.

The publication "Using Force Modulation to Image Surface Elasticities with the Atomic Force Microscope," by P. Maivald, H. J. Butt, S. A. C. Gould et al. in the magazine "Nanotechnology" 2, page 103 ff (1991), describes an atomic force microscope which allows measuring in local dependence the elasticity properties in the area of the specimen surface, in addition to the direct measurement of the topography of a specimen while keeping the average force acting on the elastic beam constant via an actuator element, by cyclically moving the specimen to and fro in relation to the nib. The elastic beam deflection is in mechanically softer areas greater than it is in mechanically harder areas. Thus, the topography as well as the elasticity properties in the near-surface area can be imaged by plotting the maximum deflections of the nib at constant force in dependence on the position of the nib.

With such an atomic force microscope it is difficult to separate the shares which in the contrast stem from the elasticity and from the topography. The modulation frequency for reciprocating the specimen is in the range of few kHz, in order for the phase shift between stimulation and deflection to be maximally low. In the described force microscope, the repetition rate is 5 kHz, of which results, in addition to the risk of a superimposition by vibrations of the mechanical structure of the acoustic microscope, a relatively long measuring time for the elasticity measurement.

The problem underlying the invention is to provide an acoustic microscope which allows measuring both the topography and elasticity of the specimen, at a high local resolution and a high signal-to-noise ratio as well as contrast, quickly and independently of one another.

SUMMARY OF THE INVENTION

This problem is inventionally solved in that the supersonic transducer is a transmitting head with which at a distance from the tip or nib, ultrasound can be coupled into the specimen, where the ultrasound has a frequency which is higher than the resonant frequency of the elastic beam or cantilever, with the nib attached to it, in that the elastic beam, the moving apparatus, the transmitting head and the specimen are rigidly joined to one another, and in that the nib deflections caused by the ultrasound coupled in can be sensed with a detection device at a consistent distance, averaged over the deflections and kept constant with the aid of a control circuit, between the nib and the surface of the specimen.

Sensing the nib deflections allows direct capture of the amplitude of the supersonically induced surface waves as a measuring signal for the elasticity measurement. By keeping a mean distance between the nib and the surface of the specimen constant with the aid of a control circuit it is possible to image the surface topography with a coordinated control signal, independently of the supersonically induced deflections of the nib. A high signal-to-noise ratio and a high contrast are achieved by the mechanically rigid joining of the components and by providing a higher supersonic frequency in relation to the resonant frequency of the elastic beam with the nib attached to it.

A first detection unit with a slow response time is favorably used in the control circuit for keeping the mean deflection of the nib constant, by means of a piezoelectric crystal. But it is also possible to obtain a control signal by low-frequency filtering from the signal of a single wide-band detector unit, which signal comprises also the supersonically induced high-frequency signal.

Ultrasound with a frequency of at least several MHz is preferably used, so that low-frequency interferences in the range of the resonant frequency of the elastic beam with the nib attached to it can be separated in a simple manner.

The elastic beam, positioning device and transmitting head are favorably joined to one another, mechanically rigidly, by means of a clamp or holder, where the resonant frequency of the holder is lower than the supersonic frequency, thus guaranteeing a sufficient mechanical stability of the acoustic microscope. Low-frequency interferences, such as for instance mechanical vibrations in the structure, have no unfavorable effect, due to measuring the nib deflection far above the inherent frequency of the elastic beam with the nib attached to it.

In one embodiment of the invention, the nib deflections are sensed by way of a deflection of a light beam reflected on the elastic beam. As a first optical detector unit, the control circuit features a bisected photodiode of an arrangement such that at a certain interactive force between nib and specimen surface the light beam incidence is centered between the two segments of the photodiode. The bandwidth of the bisected photodiode is considerably smaller than the frequency of the ultrasound coupled in, so that the high-frequency deflections of the nib escape sensing by the first detector unit.

The detector device features a second optical detector unit, which in this embodiment is formed by a single photodiode with a bandwidth of at least the ultrasound frequency, and features a smooth-edged baffle, for instance a razor blade, the two being so adjusted to one another that the baffle blocks at constant, average interactive force between nib and specimen surface, in the absence of ultrasound, substantially one-half of the light beam.

In a further embodiment, the second optical detector unit consists of a heterodyne travel time interferometer where the frequency of the light in the long interferometer arm can be shifted by means of a frequency shifting device by a predetermined amount and the two superposed output beams fall each on one photodiode. A difference demodulation amplifier allows forming the amplified difference signal of the two photodiodes, which subsequently, by demodulation of the shifting frequency, contains an output signal which matches the deflection of the nib, and thus of the elastic beam.

In another embodiment of the invention, the control circuit and the detector device are integrated in a capacitive detector where the measuring capacity is formed of the elastic beam and a needle-shaped electrode arranged opposite from it. The high-frequency changes of the measuring capacity can be separated, by a high-pass filter, from the part of the measuring capacity change separated via a low-pass filter and used as control signal. An optical structure that is sometimes sensitive to adjustment can be circumvented thereby.

Figure 2:
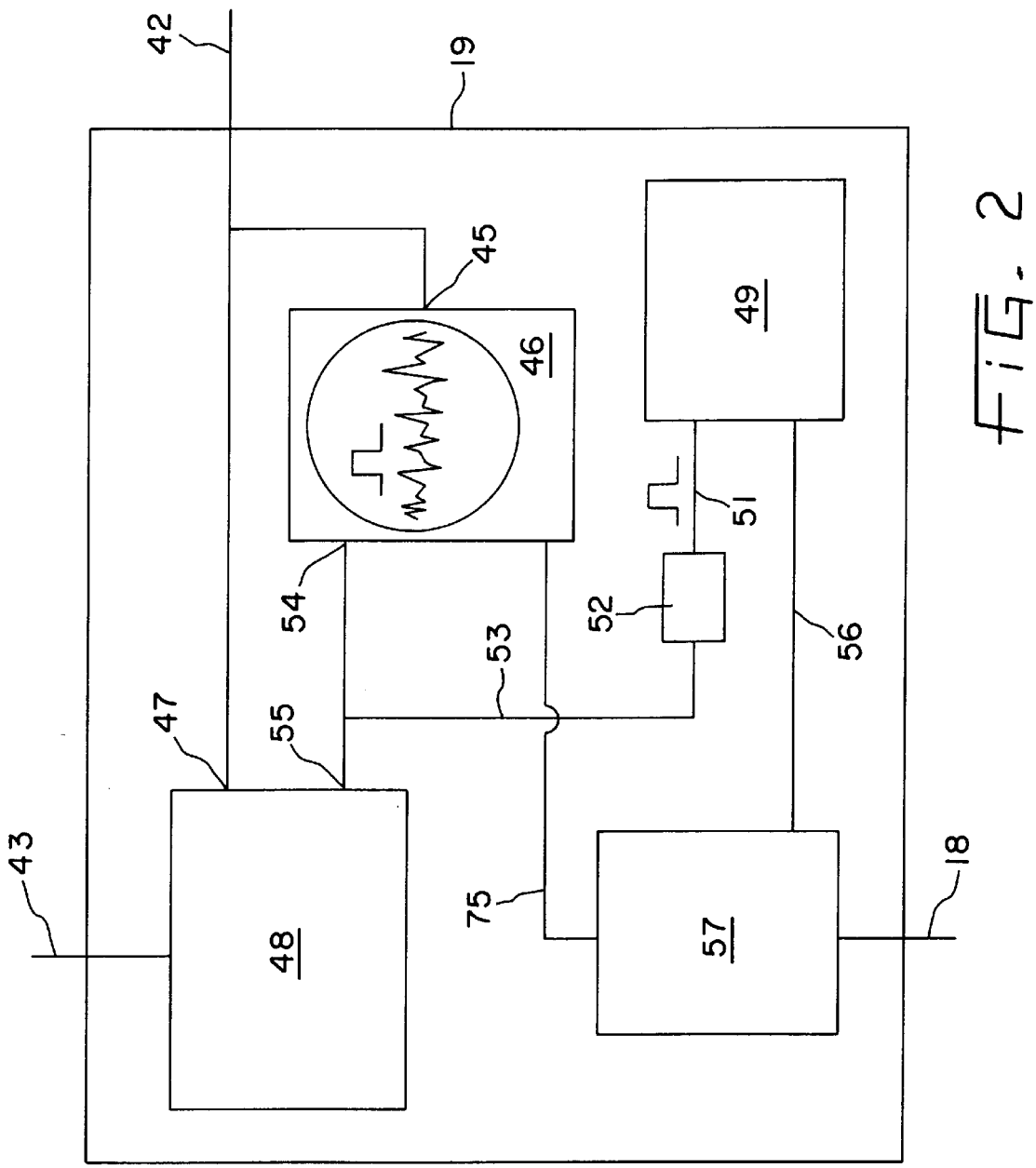
Figure 3:
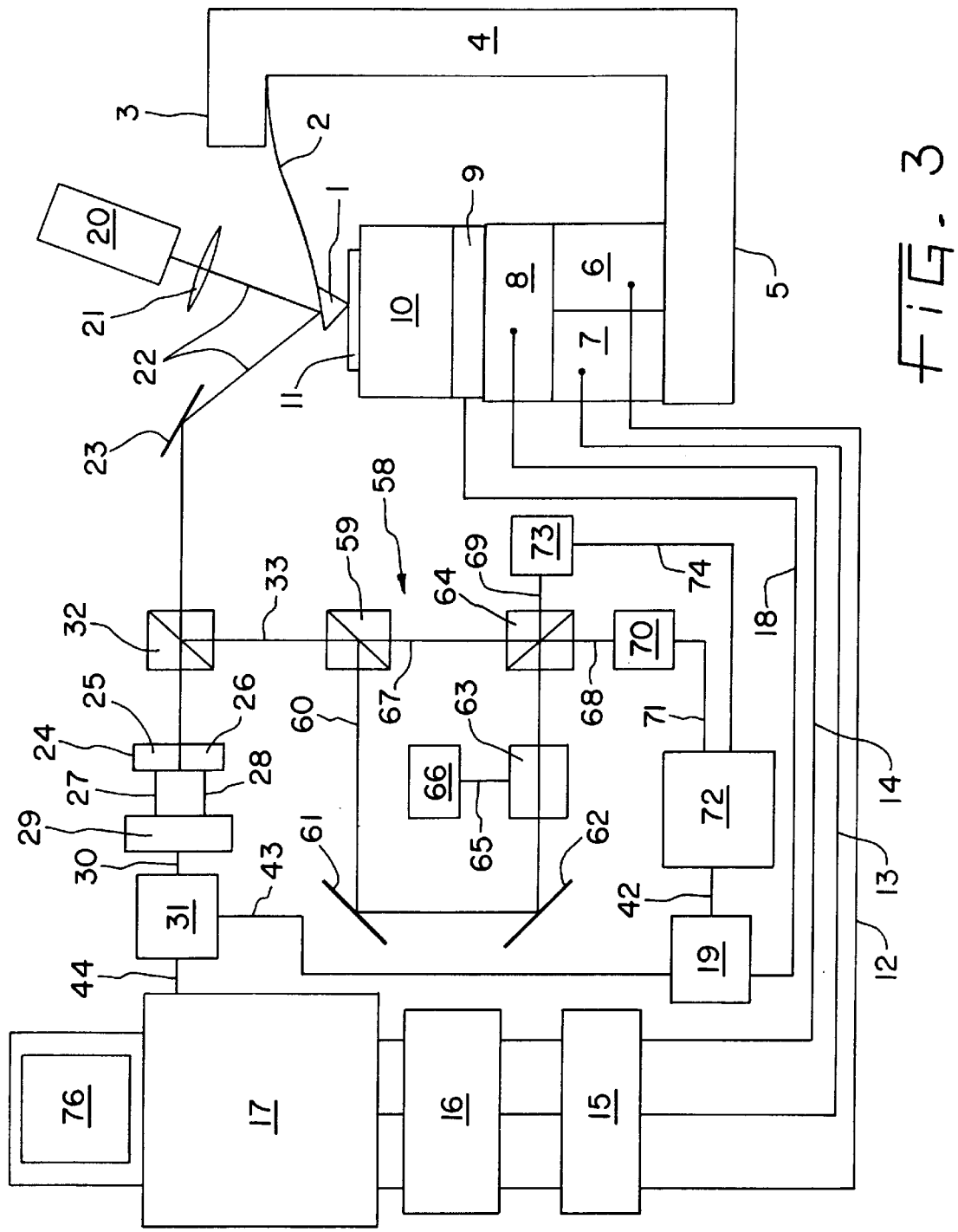
Figure 4:
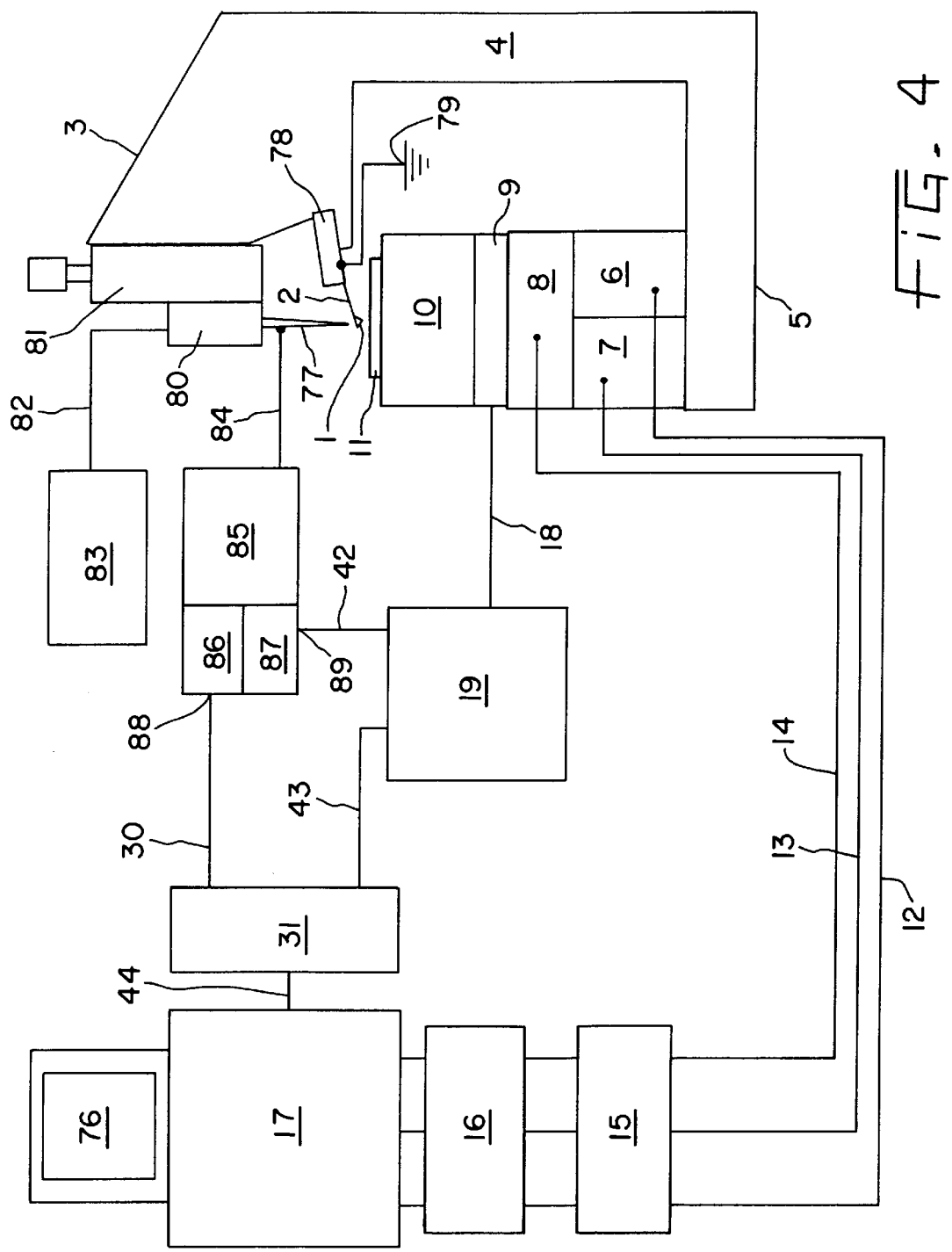

Further embodiments and advantages of the invention derive from the subclaims and the following description of figures. These show in FIG. 1, a schematic illustration of an acoustic microscope with a detection device and a control circuit with two optical detection units for sensing the topography and supersonically induced deflections of the nib;

FIG. 2, a block diagram of a transceiver unit for generation and pickup of the nib deflections;

FIG. 3, an acoustic microscope in schematic illustration, with a heterodyne travel time interferometer as a second optical detection unit for sensing the supersonically induced nib deflections; and FIG. 4, an acoustic microscope in schematic illustration, where a capacitive detection device is used to sense the supersonically induced deflections of the elastic beam.

FIG. 1 shows schematically an acoustic microscope. A tip or nib 1 is attached with its base to one end of an elastic beam or cantilever 2 of $Si_3N_4$ having a length of approximately 100 μm. In this embodiment, the nib 1 has the shape of a pyramid and at the point a radius of curvature of about 50 nm. The elastic beam 2 has a spring modulus of about 0.1 Newton per meter. With its other end, the elastic beam 2 is arranged on the upper end 3 of a mechanically rigid clamp or holder 4.

A tubular piezoelectric crystal of about 1 cm diameter and 1 mm wall thickness is applied on the base 5 of the holder 4. To perform perpendicular movements, the piezoelectric crystal features in a plane about its outer surface four electrodes which, offset 90 degrees, cover each one-fourth of the outside surface. The inside surface is coated with a grounded electrode. Two electrodes 6, 7 are schematically shown in FIG. 1. A rectangular movement in one plane can be performed by application of control voltages upon the two visible electrodes 6, 7 offset by 90 degrees. The two not visible, peripherally applied electrodes are wired to the negative voltage of the respective opposite electrode. One of the visible electrodes 6, 7—along with the pertaining invisible electrode offset by 180 degrees—serves to perform the movement in the x-direction and is referred to hereafter as x-electrode 6. Electrode 7, along with the appropriately wired opposite electrode, serves the movement in the y-direction perpendicular to the x-direction and is referred to hereafter as y-electrode 7.

One end of the tubular piezoelectric element is provided with an annular z-electrode 8, which encloses the entire circumference and serves the performance of a movement perpendicular to the plane of motion of x-electrode 6 and y-electrode 7. For better presentation, the drawing shows the size ratios distorted.

Situated on the z-electrode 8 is a transmitting head 9 with which ultrasound can be coupled in a specimen 11 through a intermediate body 10. The nib 1 rests on a surface of the specimen 11. But it may also be spaced a few hundred nanometers from the surface of the specimen 11.

The electrodes 6, 7, 8 connect each via pertaining piezoelectric control lines 12, 13, 14, a high-voltage amplifier 15 and a digital-analog converter 16 to a control and data capturing device 17. The ultrasonic transducer includes transmitting head 9 which connects via a line 18 to a transceiver 19, by means of which, as will be described in more detail farther down with reference to FIG. 2, the deflection of the nib 1 by the ultrasound can be measured. The deflections of the nib 1 amount to about 10 nanometers in the present embodiment.

Focussed by a lens 21, a laser beam 22 from a semiconductor laser diode 20 emitting at a wavelength of about 670 nm falls on the flattened free end of the elastic beam 2, to which the nib 1 is attached. The reflected part of laser beam 22 falls on a mirror 23, which directs the laser beam 22 through a beam splitter 32 and onto a bisected photodiode 24, which, as compared to the frequency of the ultrasound, is slow.

The arrangement of mirror 23 and photodiode 24 is such that the laser beam 22 falls at a specific interactive force between nib and specimen 11, with nib 1 in center position, in the center between the first element 25 and second element 26 of the bisected photodiode 24.

The photoelectric voltages of the first element 25 and second element 26 act by way of output lines 27, 28 on a standardizing amplifier 29, which standardizes and amplifies the difference between the photoelectric voltages of elements 25, 26 to their sum value. The output signal of the standardizing amplifier 29 acts via a line 30 on an input of an analog-digital converter 31 that digitizes the voltages.

The beam splitter 32 divides the laser beam 22 incident from mirror 23 at a ratio of about 1:1. The arrangement of the beam splitter 32 is such that the laser beam 33 reflected on it falls on a mirror 34 which, in turn, directs the reflected laser beam 33 through a collimating lens 35 and past a razor blade 36 onto a monocell photodiode 37 whose bandwidth at least equals the frequency of the ultrasound.

The beam splitter 32, mirror 34, collimating lens 35 and razor blade 36 are so arranged that, with centered alignment of the laser beam 22 passing through the beam splitter 32 on the bisected photodiode 24, the razor blade 36 baffles the reflected laser beam 33 substantially at center symmetry. The nonbaffled share of the reflected laser beam 33 falls on the monocell photodiode 37. The optical path lengths in this structure are in the centimeter range.

The monocell photodiode 37 is via line 38 wired to a load resistor of 50 ohms and to a protective resistor, which are illustrated as a resistance circuit 39. The monocell photodiode 37 is in the present embodiment a silicon pin diode with a rise time of about 1 nanosecond. But other light-sensitive detectors with a bandwidth greater than the frequency of the ultrasound coupled in, such as avalanche diodes, are suitable as well. The output signal of the resistance circuit 39 proceeds via a line 40 to the input of an amplifier 41 with approximately 60 decibel amplification. The output signal of amplifier 41 proceeds via a line 42 to a voltage input of the transceiver 19.

The data output of transceiver 19 connects via line 43 to a second input of the analog-digital converter 31 capable of digitizing the voltage from the transceiver 19. The data digitized by the analog-digital converter 31 can be fed, via a line 44, to the control and data capturing device 17. The digitized output signals from the standardizing amplifier 29 and transceiver 19 can be stored in a memory of the control and data capturing device 17 in contingence on the position of specimen 11. An output unit 76, for instance a monitor, is provided to output the content of the memory of the control and data capturing device 17 in the form of a color or gray value coding.

FIG. 2 shows in a block diagram the inner structure of transceiver 19. The signal of amplifier 41, in FIG. 1, prevailing on the line 42 is present on a channel 45 of an oscilloscope 46 and on the signal input 47 of a time gate integrator 48.

A supersonic transmitter 57 emits a brief pulse with about 15 nanoseconds rise time, via line 18, to the transmitting head 9. A pulse generator 49 receives at the same time a start pulse via a line 56. In response, the pulse generator 49 emits via a line 51 a rectangular pulse of adjustable duration to a delay circuit 52 that is capable of retarding the rectangular pulse in an adjustable fashion relative to the starting pulse. The retarded rectangular pulse can be fed via delay-line 53, for one, to a second channel 54 of oscilloscope 46 and, for another, to the time gate input 55 of the time gate integrator 48. The time deflection of oscilloscope 46 is triggered by the pulse generator 49 via line 75. Oscilloscope 46 allows controlling the position of the retarded rectangular pulse from the delay circuit 52 as regards the signal prevailing on channel 45.

The average amplitude prevailing on the signal input 47 can be set with the time gate integrator 48 while the high level of the retarded rectangular pulse from the pulse generator 49 is present on the time gate input 55. The average amplitude value can be fed via line 43 to the analog-digital converter 31 of FIG. 1 for digitizing.

The repetition rate of the supersonic transmitter 57 is such that the supersonic amplitude values will be updated at least once in each position of the specimen 11, before the control and data capturing device 17 reads a new amplitude value. In the present embodiment, the supersonic repetition rate is about 1 kHz, so that up to a read-in frequency of about 500 Hz there is assurance that at least one supersonic pulse will be transmitted at each position of the specimen 11.

As previously mentioned, the mean interactive force between nib 1 and specimen 11 must be kept constant during measurement. This can be accomplished in that, in a control circuit, the part of laser beam 22 transmitted through the beam splitter 32 is held centered, via control and data capturing device 17 and by appropriate feedback loop adjustment of the z-electrode 8, between the first element 25 and second element 26 of the bisected photodiode 24. At positive or negative changes of the output level of standardizing amplifier 29, the voltage on the piezoelectric control line 14 to the z-electrode 8 allows adjustment such that the-output voltage of the standardizing amplifier 29 approaches neutral value. In contingence on the x- and y-positions of specimen 11, the control voltage for the z-electrode 8 provides an image of the topography of specimen 11.

The frequency of the ultrasound is adjustable between about 5 MHz and about 100 MHz, ranges thus far above the resonant frequency of several KHz of the elastic beam 2 with the nib 1 as used in the present embodiment.

Concerned with the ultrasound coupled in, in the present embodiment, are longitudinal waves, so that the surface of specimen 11 performs normal vibrations. These normal vibrations result in a high-frequency deflection of the elastic beam 2, which, however, escape detection due to the insufficient bandwidth of the slow, bisected photodiode 24, but result in the monocell photodiode 37 with a bandwidth in the megahertz range, due to baffling part of the reflected laser beam 33 with the razor blade 36, in a measuring signal.

The delay circuit 52 in this embodiment is adjusted such that the average amplitude of the first high-frequency deflection of elastic beam 2, in response to the surface vibration of specimen 11, can be selected in the time gate integrator 48. Upon storing a value for the deflection of nib 1, the specimen 11 may be positioned on the x-electrode 6 and y-electrode 7 at the next measuring point, by means of appropriate output signals of the control and data capturing device 17, followed by the next ultrasound measuring cycle.

During rasterization of the surface of specimen 11 across the predetermined measuring area, the control voltages of the z-electrode 8 for imaging the topography of the surface of specimen 11, matched to location, are displayed on the output unit 76, along with a location-matched representation of the supersonically induced deflection of nib 1 by way of the respective measuring values. A customary gray value or color coding is preferably chosen for this representation. In this fashion, both an image of the topography of the surface of specimen 11 and an image of the amplitudes of the supersonic waves at the surface of specimen 11, matching the elasticity properties of the specimen surface, can be generated simultaneously in metrologically independent fashion.

For metrological scanning of other time ranges of the emitted ultrasound it is possible to timewise vary the time gate by means of the delay circuit 52. This is necessary especially when the intermediate body 10 has been changed along with the passage time.

FIG. 3 illustrates schematically a further embodiment of an acoustic microscope where the components corresponding to those of FIG. 1 are referenced identically and not illustrated hereafter in any detail. In the embodiment according to FIG. 3, the laser beam 33 reflected by the beam splitter 32 is coupled into a heterodyne travel time interferometer 58. The reflected laser beam 33 falls on an input beam splitter 59 which couples approximately one-half of the incident intensity into the long arm 60 of the heterodyne travel time interferometer 58.

The long arm 60 contains two mirrors 61, 62 which direct the light in the long arm 60 through a Bragg cell 63 operating on the basis of the acousto-optic effect onto an output beam splitter 64. The arrangement of the mirrors 61, 62 and of the Brag cell 63 is such that frequency-shifted output light of first-order refraction, of the Bragg cell 63, falls on the output beam splitter 64. The Brag cell 63 connects via a line 65 to an activation circuit 66, by means of which the amount of frequency shift has in the present embodiment been set to about 80 MHz.

The short arm 67 of the heterodyne travel time interferometer 58 is formed by the share of the laser beam 33 transmitted through the input beam splitter 59, of about one-half its intensity. The light pencils of the long arm 60 and short arm 67 are collinearly superimposed in the interference beams 68, 69 through the output beam splitter 64.

The first interference beam 68 falls on a first interference photodiode 70, the output signal of which acts via line 71 on a first input of a difference demodulation amplifier 72. The second interference beam 69 falls on a second interference photodiode 73, the output signal of which acts via line 74 on a second input of the difference demodulation amplifier 72.

Because of the difference in travel time of the light between the short arm 67 and the long arm 60, the output signals of the interference photodiodes 70, 73 contain in customary fashion phase modulations that are proportional to the deflection differences of the nib 1. The travel difference between arms 60, 67 is preferably so chosen that the sensitivity of the interferometer to the incident supersonic frequency is maximal, meaning that the difference in arm length equals about the speed of light divided by twice the supersonic frequency multiplied by the index of refraction.

The difference demodulation amplifier 72 is capable of forming the difference between the output signal of the first interference photodiode 70 and the second interference photodiode 73; this difference signal allows decoupling from low-frequency interferences, by the frequency shift in the Bragg cell 63 with subsequent demodulation. This makes it possible to even out, e.g., intensity fluctuations in the reflected beam 33 or low-frequency mechanical disturbances. Moreover, the difference signal is suited for amplification in the difference demodulation amplifier 72 and acts by way of line 42 on the time gate integrator 48 of transceiver 19.

In a modified embodiment, the heterodyne travel time interferometer 58 has been substituted by an actively stabilized fiber-optic travel time interferometer. The stabilized interferometer features in its long arm a phase shifter which in a control circuit connects via a line to the difference amplifier, so that changes of the optical path length can be evened out. Coupling in and out, the same as in the embodiment illustrated in FIG. 3, is effected using the heterodyne travel time interferometer.

FIG. 4 illustrates a further embodiment of the invention where the components corresponding to those in FIG. 1 and 3 are referenced identically and will not be described in any detail hereafter. In the embodiment relative to FIG. 4, the deflections of nib 1 can be detected by means of a capacitive detector device. Said device has a measuring capacity which is formed by the metallically coated back of the elastic beam 2 and a stylus type opposite electrode 77, the point of which is aligned on the elastic beam 2. The latter is attached to an electrically conducting holder 78 that connects to a ground 79.

The opposite electrode 77 is mechanically attached to a piezoelectric element 80 and electrically decoupled from it. Said piezoelectric element 80 is mounted on a mechanical positioning table 81 which, in turn, is mounted on the holder 4. The piezoelectric element 80 is acted upon by a voltage from an adjustable power supply 83, by way of line 82. The opposite electrode 77 allows positioning at a distance above the elastic beam 2, with rough positioning through mechanical adjustment of the positioning table 81, and precision positioning by way of modifying the supply voltage of the piezoelectric element 80.

The opposite electrode 77 connects electrically via a line 84 to a capacity measuring circuit 85. The measuring capacity is integrated in an oscillating circuit of the capacitive measuring circuit 85, which is stimulated by an oscillator vibrating at about 915 MHz. The oscillator frequency is so selected that it is in the steepest area of the flank of the resonance curve of the oscillating circuit. Changes in measuring capacity, by deflections of nib 1 and thus of elastic beam 2, result in a change of the resonant frequency of the oscillating circuit, and thus of the amplitude stimulated by the oscillator. These amplitude changes are splittable in a low-frequency and a high-frequency share by a low-pass filter 86 and a high-pass filter 87.

The low-pass filter 86 has a passband up to about 20 kHz, while the passband of the high-pass filter 87 starts at about one-half the supersonic frequency value. This makes it possible to tap the slow deflections of the nib 1, produced by topography changes of the surface of specimen 11, at a low-frequency output 88 while tapping the high-frequency supersonically induced deflections of the nib 1 at a high-frequency output 89.

The signal prevailing on the low-frequency output 88 can be passed via line 30 to the analog-digital converter 31 and serves as a control signal for keeping the average distance between the surface of specimen 11 and nib 1 constant. The signal prevailing on the high-frequency output 89 is suited for coupling into the transceiver 19 via line 42. The further data processing proceeds as described in conjunction with FIG. 1, 2, and 3.

We claim:

1. An acoustic microscope for the examination of a specimen, with a tip fastened to a cantilever, said tip being in the surface-near-zone of the specimen, said microscope comprising an ultrasonic transducer, a scanning device for positioning the specimen relative to the tip, and with a device for control and data acquisition, wherein a) the ultrasonic transducer includes a transmitter with means for providing ultrasound coupled to the specimen, b) the ultrasound has a frequency which exceeds the lowest resonance frequency of the cantilever with the tip fixed to the cantilever, c) the cantilever, a clamp with a resonance frequency lower than the ultrasonic frequency, the scanning device, the transmitter, and the specimen are mechanically rigidly coupled to one another, and d) with a detection unit installed which measures the deflections of the tip caused by the topography of the specimen, the deflections being of lower frequency in relation to the ultrasonic frequency in a first detection signal, and the detection unit also measuring high-frequency displacements of the tip caused by the ultrasound in the specimen in a second detection signal, and means for maintaining a constant distance between the tip and the surface of the specimen by utilizing a feedback loop in the control and data acquisition device, the feedback loop serving to average the first detection signal using a time large as compared to the period of the ultrasonic frequency and with a scanning rate small as compared to the ultrasonic frequency, and a light beam reflected by the cantilever can be coupled, via optical devices for beam deflection, into a detection unit which comprises a first optical detection unit connected with the feedback loop and a second optical detection unit for generation of the second detection signal, said second detection unit contains a heterodyne time-of-flight interferometer whose long reference arm contains a frequency shifter in order to shift the frequency of the light-beam in the long reference arm.

2. An acoustic microscope, as defined in claim 1, characterized in that the interfering beams of the heterodyne time-of-flight interferometer are directed each onto a light-sensitive detector whose output signals are subtracted from one another in a difference demodulation amplifier, and demodulated from the frequency of the frequency shifter and amplified.

* * * * *